(12) United States Patent
Suzuki et al.

(10) Patent No.: US 9,393,444 B2
(45) Date of Patent: Jul. 19, 2016

(54) TREATMENT PLANNING DEVICE, TREATMENT PLANNING METHOD, AND PROGRAM THEREFOR

(71) Applicants: MITSUBISHI HEAVY INDUSTRIES, LTD., Tokyo (JP); KYOTO UNIVERSITY, Kyoto (JP)

(72) Inventors: Yasunobu Suzuki, Tokyo (JP); Masahiro Hiraoka, Kyoto (JP); Yukinori Matsuo, Kyoto (JP)

(73) Assignees: MITSUBISHI HEAVY INDUSTRIES, LTD., Tokyo (JP); KYOTO UNIVERSITY, Kyoto (JP)

(*) Notice: Subject to any disclaimer, the term of this patent is extended or adjusted under 35 U.S.C. 154(b) by 78 days.

(21) Appl. No.: 14/379,906

(22) PCT Filed: Feb. 27, 2013

(86) PCT No.: PCT/JP2013/055076
§ 371 (c)(1),
(2) Date: Aug. 20, 2014

(87) PCT Pub. No.: WO2013/129450
PCT Pub. Date: Sep. 6, 2013

(65) Prior Publication Data
US 2015/0065779 A1    Mar. 5, 2015

(30) Foreign Application Priority Data
Feb. 28, 2012    (JP) .................................. 2012-042171

(51) Int. Cl.
*A61N 5/10* (2006.01)

(52) U.S. Cl.
CPC ............ *A61N 5/1037* (2013.01); *A61N 5/1031* (2013.01); *A61N 5/1039* (2013.01); *A61N 5/1049* (2013.01); *A61N 5/1067* (2013.01); *A61N 5/1082* (2013.01); *A61N 2005/1061* (2013.01)

(58) Field of Classification Search
CPC ................... A61N 5/1049; A61N 2005/1091; A61N 5/1042; A61N 5/103; A61N 5/1031; A61N 5/1048; A61N 5/1037
See application file for complete search history.

(56) References Cited

U.S. PATENT DOCUMENTS

2006/0074292 A1* 4/2006 Thomson ............. A61N 5/1039
                                                                    600/411
2008/0081991 A1   4/2008 West et al.
(Continued)

FOREIGN PATENT DOCUMENTS

| CN | 101032651 | 9/2007 |
|----|-----------|--------|
| CN | 101076282 | 11/2007 |

(Continued)

OTHER PUBLICATIONS

International Search Report issued Apr. 16, 2013 in corresponding International Application No. PCT/JP2013/055076.
(Continued)

*Primary Examiner* — Hoon Song
(74) *Attorney, Agent, or Firm* — Wenderoth, Lind & Ponack, L.L.P.

(57) ABSTRACT

This treatment planning device calculates position information for specific locations for a plurality of times corresponding to a time course on the basis of the positions of markers positioned in the vicinity of the specific locations, and generates a three-dimensional range for the specific locations for each of the plurality of times. In addition, the treatment planning device generates representative range information, which represents a range that includes the entire three-dimensional ranges for the specific locations for each of the plurality of times, tracks the position information for the specific locations for each of the plurality of times, and calculates the amount of radiation to be emitted in the range for the specific locations represented by representative range information when radiation is emitted for a prescribed time period in the range for the specific locations represented by the representative range information.

5 Claims, 9 Drawing Sheets

(56) References Cited

U.S. PATENT DOCUMENTS

2009/0041188 A1    2/2009    Keall et al.
2011/0044429 A1    2/2011    Takahashi et al.

FOREIGN PATENT DOCUMENTS

| | | |
|---|---|---|
| CN | 101861185 | 10/2010 |
| JP | 2002-186678 | 7/2002 |
| JP | 2007-236760 | 9/2007 |
| JP | 2008-80131 | 4/2008 |
| WO | 2009/072618 | 6/2009 |

OTHER PUBLICATIONS

Translation of Written Opinion of the International Searching Authority issued Apr. 16, 2013 in corresponding International Application No. PCT/JP2013/055076.

Office Action issued Dec. 2, 2015 in corresponding Chinese Application No. 201380010659.9 (with English translation).

\* cited by examiner

| | DISPLACEMENT AMOUNT (x) OF SPECIFIC PORTION | DISPLACEMENT AMOUNT (y) OF MARKER |
|---|---|---|
| $A_{t1}$ | $x_1$ | $y_1$ |
| $A_{t2}$ | $x_2$ | $y_2$ |
| $A_{t3}$ | $x_3$ | $y_3$ |

TREATMENT PLANNING DEVICE, TREATMENT PLANNING METHOD, AND PROGRAM THEREFOR

TECHNICAL FIELD

The present invention relates to a treatment planning device, a treatment planning method, and a program used to specify a position of a specific portion within a subject and computing a radiation dose to be radiated to the specific portion.

Priority is claimed on Japanese Patent Application No. 2012-042171, filed Feb. 28, 2012, the content of which is incorporated herein by reference.

BACKGROUND ART

Radiotherapy equipment used to perform treatment by irradiating an affected part within a subject with radiation is known. In radiotherapy, it is necessary to define a radiation dose to be radiated to a specific portion (affected part) and a position of a radiation source using a treatment planning device.

Here, a position of the affected part (specific portion) varies as time passes due to the subject's respiration or the like. Accordingly, it was also necessary to vary an irradiation position of radiation therewith and perform tracking irradiation of the specific portion. As technology used to perform tracking irradiation of a specific portion with radiation, technology for embedding a marker inside the subject, pre-measuring relative positions of the marker and the affected part using a computed tomography (CT) image or the like, and estimating the position of the affected part from relative positions to positions of a plurality of markers after a predetermined time is disclosed in Patent Literature 1.

In addition, technology used to compute a radiation dose radiated to the specific portion is disclosed in Patent Literature 2.

PRIOR ART LITERATURE

Patent Literature

[Patent Literature 1]
  Japanese Unexamined Patent Application, First Publication No. 2007-236760
[Patent Literature 2]
  PCT International Publication No. WO 2009/072618

DISCLOSURE OF INVENTION

Problems to be Solved by the Invention

However, it is difficult to accurately measure radiation dose of the specific portion that moves and changes range within a subject as time passes using any of the above-described technologies.

Therefore, an objective of some aspects of the present invention is to provide a treatment planning device, a treatment planning method, and a program that enable radiation dose of the specific portion that moves changes range within a subject as time passes.

Means for Solving the Problems

In order to achieve the aforementioned objective, one aspect of the present invention is a treatment planning device used to specify a position of a specific portion within a subject and computing a radiation dose to be radiated to the specific portion, the treatment planning device including: a specific portion position computation unit configured to compute position information of the specific portion at a plurality of times as time passes based on the positions of a plurality of markers located in the vicinity of the specific portion; a specific portion range information generation unit configured to generate a three-dimensional range of the specific portion at each of the plurality of times; a specific portion representative range information generation unit configured to generate representative range information representing a range including all the three-dimensional ranges of the specific portion at each of the plurality of times when the position information of the specific portion at each of the plurality of times is designated as the same reference point; and a radiation dose computation unit configured to compute a radiation dose to be radiated to the range of the specific portion represented by the representative range information when radiation is radiated to the range of the specific portion represented by the representative range information for a predetermined time by following the position information of the specific portion at the plurality of times.

In addition, in the treatment planning device which is the one aspect of the present invention, the specific portion position computation unit includes: a reference position information acquisition unit configured to acquire reference position information representing a position within the subject at a reference time of each of the specific portion and the plurality of markers; a representative point reference position information computation unit configured to generate reference position information representing a position within the subject at the reference time of a representative point of the plurality of markers from the reference position information of the plurality of markers; a relative position information computation unit configured to generate relative position information of a position represented by the reference position information of the specific portion using a position represented by the reference position information of the representative point as a base point; a marker position information acquisition unit configured to acquire position information of the plurality of markers within the subject at another time different from the reference time; a representative point position information computation unit configured to generate position information of the representative point within the subject at the other time of the plurality of markers from the position information of the plurality of markers; and a specific portion position information computation unit configured to generate position information of the specific portion at the other time from the position information of the representative point and the relative position information.

In addition, in the treatment planning device which is the one aspect of the present invention, the representative point reference position information computation unit specifies a weight coefficient for each of the plurality of markers and generates the reference position information of the representative point based on the position information of the plurality of markers weighted by the weight coefficient, and the representative point position information computation unit generates the position information of the representative point based on the position information of the plurality of markers weighted by the weight coefficient.

In addition, another aspect of the present invention is a processing method of a treatment planning device used to specify a position of a specific portion within a subject and computing a radiation dose to be radiated to the specific portion, the processing method including: computing, by a specific portion position computation unit, position information of the specific portion at a plurality of times as time passes based on positions of a plurality of markers located in the vicinity of the specific portion; generating, by a specific portion range information generation unit, a three-dimensional range of the specific portion at each of the plurality of times; generating, by a specific portion representative range information generation unit, representative range information representing a range including all the three-dimensional ranges of the specific portion at each of the plurality of times when the position information of the specific portion at each of the plurality of times is designated as the same reference point; and computing, by a radiation dose computation unit, a radiation dose to be radiated to the range of the specific portion represented by the representative range information when radiation is radiated to the range of the specific portion represented by the representative range information for a predetermined time by following the position information of the specific portion at a plurality of times.

In addition, still another aspect of the present invention is a program that runs a computer in a treatment planning device used to specify a position of a specific portion within a subject and computing a radiation dose to be radiated to the specific portion to function as: a specific portion position computation means configured to compute position information of the specific portion at a plurality of times as time passes based on positions of a plurality of markers located in the vicinity of the specific portion; a specific portion range information generation means configured to generate a three-dimensional range of the specific portion at each of the plurality of times; a specific portion representative range information generation means configured to generate representative range information representing a range including all the three-dimensional ranges of the specific portion at each of the plurality of times when the position information of the specific portion at each of the plurality of times is designated as the same reference point; and a radiation dose computation means configured to compute a radiation dose to be radiated to the range of the specific portion represented by the representative range information when radiation is radiated to the range of the specific portion represented by the representative range information for a predetermined time by following the position information of the specific portion at the plurality of times.

Effects of the Invention

According to some aspects of the present invention, it is possible to more accurately compute a radiation dose when an irradiation range is set so that radiation exposure outside of the specific portion does not occur for a specific portion.

PREFERRED EMBODIMENTS FOR CARRYING OUT THE INVENTION

Hereinafter, a treatment planning device according to an embodiment of the present invention will be described with reference to the drawings.

Figure 1:
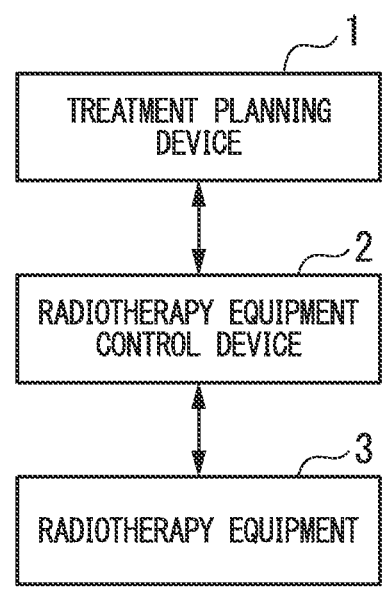
FIG. 1 is a diagram illustrating a radiotherapy system configured to include a treatment planning device.

FIG. 1 is a diagram illustrating a radiotherapy system configured to include the treatment planning device according to the embodiment.

In FIG. 1, reference numeral 1 represents the treatment planning device. In addition, reference numeral 2 represents a radiotherapy equipment control device, and reference numeral 3 represents radiotherapy equipment. A communication connection is established between the treatment planning device 1 and the radiotherapy equipment control device 2. In addition, a communication connection is established between the radiotherapy equipment control device 2 and the radiotherapy equipment 3.

Here, the treatment planning device 1 is a device used to determine position information of a specific portion such as an affected part located within a subject such as a human or to compute a radiation dose.

In addition, the radiotherapy equipment control device 2 is a device used to control the radiotherapy equipment based on plan information generated by the treatment planning device 1.

In addition, the radiotherapy equipment 3 is a device used to radiate radiation that passes through a position represented by position information of the specific portion based on an instruction from the radiotherapy equipment control device 2.

Figure 2:
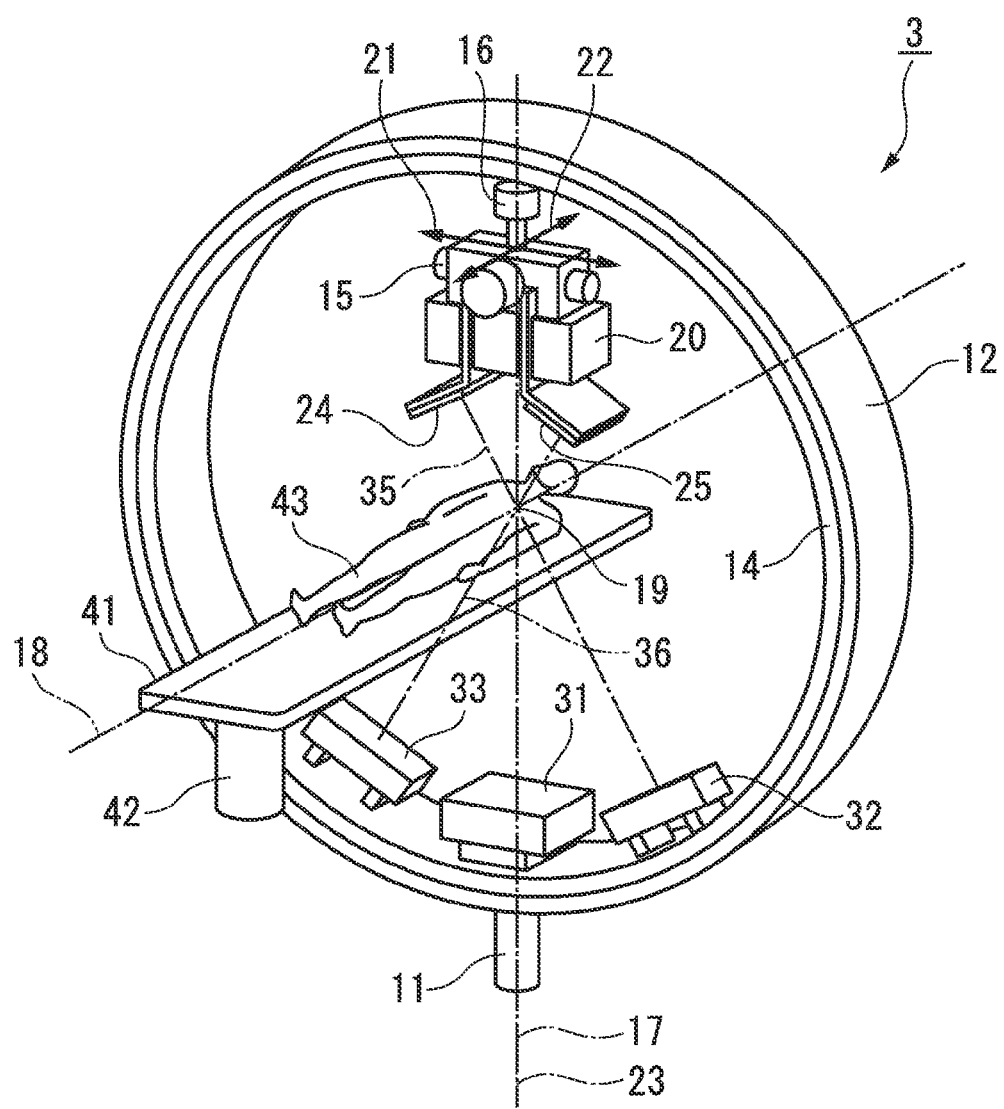
FIG. 2 is a diagram illustrating radiotherapy equipment 3.

FIG. 2 is a diagram illustrating the radiotherapy equipment 3.

The radiotherapy equipment 3 is provided with a turning drive device 11, an O ring 12, a traveling gantry 14, a swing mechanism 15, and a therapeutic radiation irradiation device 16. The turning drive device 11 supports the O ring 12 on a base so that the O ring 12 is rotatable around a rotation axis 17, and is controlled by the radiotherapy equipment control device 2 to rotate the O ring 12 around the rotation axis 17. The rotation axis 17 is parallel to a vertical direction. The O ring 12 is formed in a ring shape centered on a rotation axis 18, and supports the traveling gantry 14 so that the traveling gantry 14 is rotatable around the rotation axis 18. The rotation axis 18 is perpendicular to the vertical direction, and passes through an isocenter 19 included in the rotation axis 17. The rotation axis 18 is further fixed with respect to the O ring 12, that is, rotates around the rotation axis 17 along with the O ring 12. The traveling gantry 14 is formed in a ring shape centered on the rotation axis 18, and arranged to be concentric with the ring of the O ring 12. The radiotherapy equipment 3 is further provided with a traveling drive device (not illustrated). The traveling drive device is controlled by the radiotherapy equipment control device 2 to rotate the traveling gantry 14 around the rotation axis 18.

The swing mechanism 15 is fixed on internal side of the ring of the traveling gantry 14 to support the therapeutic radiation irradiation device 16 to the traveling gantry 14 so that the therapeutic radiation irradiation device 16 is arranged inside the traveling gantry 14. The swing mechanism 15 has a pan axis 21 and a tilt axis 22. The tilt axis 22 is fixed with respect to the traveling gantry 14 and is parallel to the rotation axis 18 without intersecting the rotation axis 18. The pan axis 21 is orthogonal to the tilt axis 22. The swing mechanism 15 is controlled by the radiotherapy equipment control device 2 to rotate the therapeutic radiation irradiation device 16 around the pan axis 21 and rotate the therapeutic radiation irradiation device 16 around the tilt axis 22.

The therapeutic radiation irradiation device 16 is controlled by the radiotherapy equipment control device 2 to radiate therapeutic radiation 23. The therapeutic radiation 23 is radiated substantially along a straight line passing through an intersection at which the pan axis 21 and the tilt axis 22 intersect. The therapeutic radiation 23 is formed to have a uniform strength distribution. The therapeutic radiation irradiation device 16 includes a multi-leaf collimator (MLC) 20. The MLC 20 is controlled by the radiotherapy equipment control device 2, and changes a shape of a radiation field when the therapeutic radiation 23 is radiated to the patient by shielding part of the therapeutic radiation 23.

As the therapeutic radiation irradiation device 16 is supported on the traveling gantry 14 in this manner, the therapeutic radiation 23 constantly approximately passes through the isocenter 19 even when the O ring 12 is rotated by the turning drive device 11 or the traveling gantry 14 is rotated by the traveling drive device once adjustment is performed by the swing mechanism 15 so that the therapeutic radiation irradiation device 16 is directed toward the isocenter 19. That is, the radiation of the therapeutic radiation 23 from an arbitrary direction to the isocenter 19 is enabled by performing traveling and/or turning.

The radiotherapy equipment 3 is further provided with a plurality of imager systems. That is, the radiotherapy equipment 3 is provided with diagnostic X-ray sources 24 and 25 and sensor arrays 32 and 33.

The diagnostic X-ray source 24 is supported on the traveling gantry 14. The diagnostic X-ray source 24 is arranged inside the ring of the traveling gantry 14 and arranged at a position at which an angle formed by a line segment connecting the isocenter 19 and the diagnostic X-ray source 24 and a line segment connecting the isocenter 19 and the therapeutic radiation irradiation device 16 is an acute angle. The diagnostic X-ray source 24 is controlled by the radiotherapy equipment control device 2 to radiate diagnostic X-rays 35 toward the isocenter 19. The diagnostic X-rays 35 are radiated from one point included in the diagnostic X-ray source 24, and are cone beams of a conical shape with the one point serving as a vertex. The diagnostic X-ray source 25 is supported on the traveling gantry 14. The diagnostic X-ray source 25 is arranged inside the ring of the traveling gantry 14 and arranged at a position at which an angle formed by a line segment connecting the isocenter 19 and the diagnostic X-ray source 25 and a line segment connecting the isocenter 19 and the therapeutic radiation irradiation device 16 is an acute angle. The diagnostic X-ray source 25 is controlled by the radiotherapy equipment control device 2 to radiate diagnostic X-rays 36 toward the isocenter 19. The diagnostic X-rays 36 are radiated from one point included in the diagnostic X-ray source 25, and are cone beams of a conical shape with the one point serving as a vertex.

The sensor array 32 is supported on the traveling gantry 14. The sensor array 32 receives the diagnostic X-rays 35 radiated by the diagnostic X-ray source 24 and transmitted through a subject around the isocenter 19 to generate a transmission image of the subject. The sensor array 33 is supported on the traveling gantry 14. The sensor array 33 receives the diagnostic X-rays 36 radiated by the diagnostic X-ray source 25 and transmitted through the subject around the isocenter 19 to generate a transmission image of the subject. Examples of flat panel detectors (FPDs) and X-ray image intensifiers (IIs) are shown as the sensor arrays 32 and 33.

The radiotherapy equipment 3 is further provided with a sensor array 31. The sensor array 31 is arranged so that a line segment connecting the sensor array 31 and the therapeutic radiation irradiation device 16 passes through the isocenter 19, and is fixed inside the ring of the traveling gantry 14. The sensor array 31 receives light of the therapeutic radiation 23 radiated by the therapeutic radiation irradiation device 16 and transmitted through the subject around the isocenter 19 to generate a transmission image of the subject. Examples of an FPD and an X-ray II are shown as the sensor array 31.

The radiotherapy equipment 3 is further provided with a couch 41 and a couch drive device 42. The couch 41 is used for a patient 43 to be treated by the radiotherapy system to lie on.

The couch 41 is provided with a fixing tool (not illustrated). This fixing tool fixes the patient to the couch 41 so that the patient does not move. The couch drive device 42 supports the couch 41 on the base and is controlled by the radiotherapy equipment control device 2 to move the couch 41.

Figure 3:
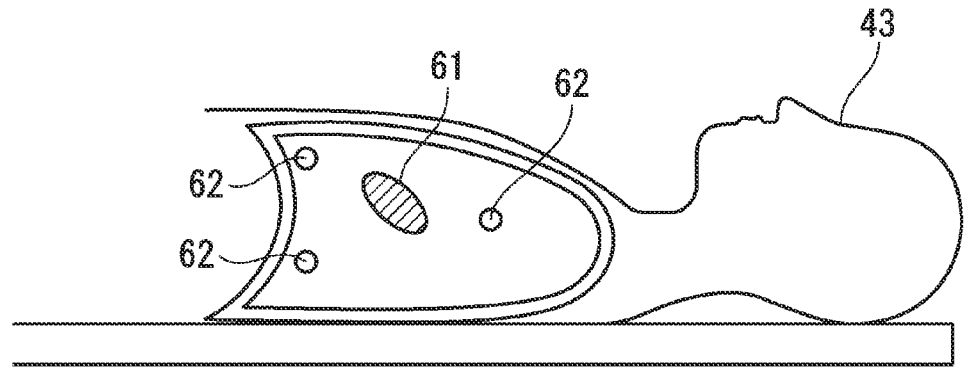
FIG. 3 is a diagram illustrating a patient (subject) 43.

FIG. 3 illustrates a patient (subject) 43.

The patient 43 has a specific portion 61 inside a body. The specific portion 61 represents an affected part of the patient 43, and is a portion to be irradiated with the therapeutic radiation 23. As the specific portion 61, part of a lung is illustrated. In addition, a plurality of markers 62 are arranged within a body of the patient 43.

In order to detect a position of the specific portion 61, the marker 62 is intended to stay at a predetermined position for the specific portion 61, and a small piece of metal embedded in the vicinity of the specific portion 61, for example, gold, is used. The marker 62 may be embedded by injection into the subject from a needle of a syringe and may be embedded according to another method such as surgery.

Figure 4:
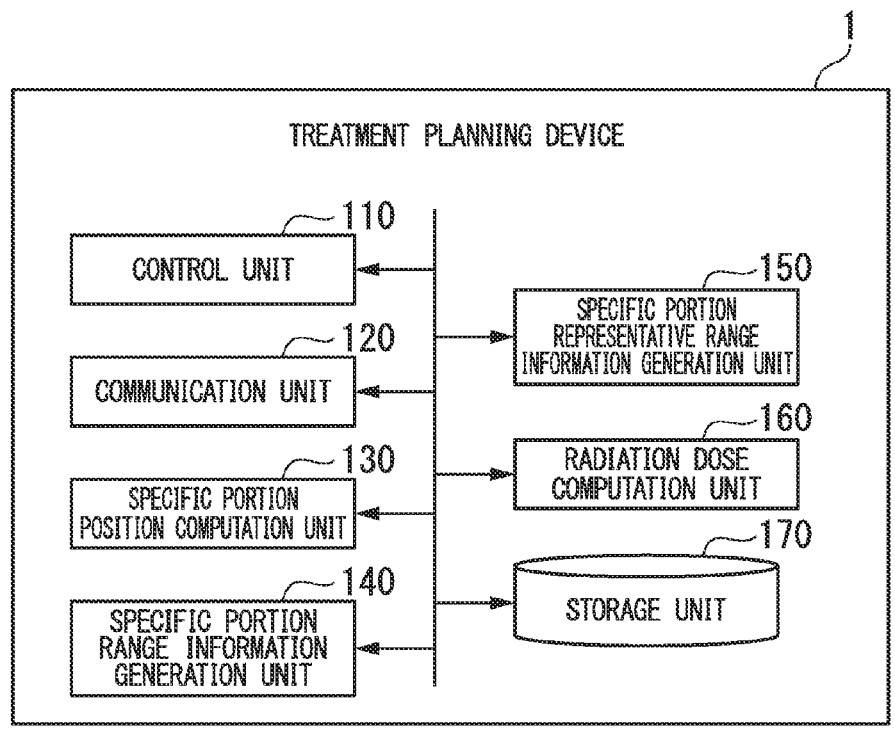
FIG. 4 is a functional block diagram of the treatment planning device 1.

FIG. 4 is a functional block diagram of the treatment planning device 1.

As illustrated in FIG. 4, the treatment planning device 1 includes processing units of a control unit 110, a communication unit 120, a specific portion position computation unit 130, a specific portion range information generation unit 140, a specific portion representative range information generation unit 150, a radiation dose computation unit 160 and a storage unit 170 used to store information to be used in a process.

The control unit 110 controls the processing units.

The communication unit 120 is the processing unit used to communicate with the radiotherapy equipment control device 2.

The specific portion position computation unit 130 is the processing unit used to compute position information of a specific portion at a plurality of times as time passes based on a position of a marker located in the vicinity of the specific portion.

The specific portion range information generation unit 140 is the processing unit used to generate three-dimensional ranges of the specific portion at each of a plurality of times.

The specific portion representative range information generation unit 150 is the processing unit used to generate representative range information representing a range including all the three-dimensional ranges of the specific portion at each of the plurality of times when the position information of the specific portion at each of the plurality of times is designated as the same reference point.

The radiation dose computation unit 160 is the processing unit used to compute a radiation dose to be radiated to the range of the specific portion represented by the representative range information when radiation is radiated to the range of the specific portion represented by the representative range information for a predetermined time by following the position information of the specific portion at each of a plurality of times.

Figure 5:
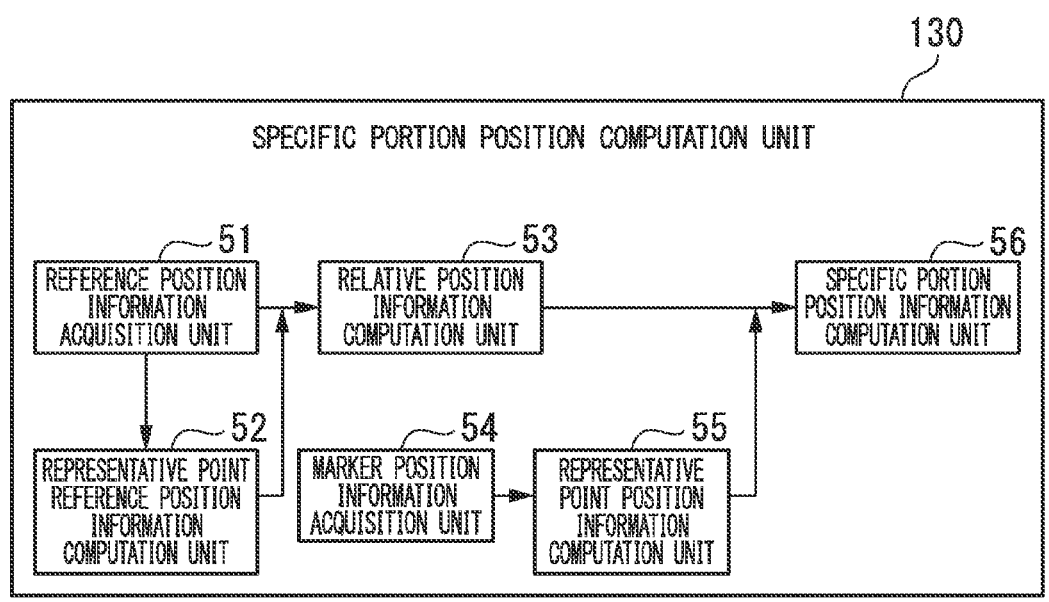
FIG. 5 is a functional block diagram of a specific portion position computation unit 130.

FIG. 5 is a functional block diagram of the specific portion position computation unit 130.

As illustrated in FIG. 5, the specific portion position computation unit 130 includes a reference position information acquisition unit 51, a representative point reference position information computation unit 52, a relative position information computation unit 53, a marker position information acquisition unit 54, a representative point position information computation unit 55, and a specific portion position information computation unit 56.

The reference position information acquisition unit 51 acquires reference position information representing positions of the specific portion 61 and the plurality of markers 62 within a body of the patient 43 at a reference time. The reference position information acquisition unit 51 acquires the reference position information from a three-dimensional CT image generated based on a transmission image captured by the radiotherapy equipment 3. The reference position information of the specific portion 61 and the plurality of markers 62 is represented as three-dimensional coordinates.

The representative point reference position information computation unit 52 generates representative point reference position information representing a position within the subject of a representative point of the plurality of markers 62 at the reference time.

At this time, the representative point reference position information computation unit 52 specifies a weight coefficient for each of the plurality of markers 62. In addition, the representative point reference position information computation unit 52 computes a reference position of the representative point by multiplying three-dimensional coordinates represented by the reference position information for each of the plurality of markers 62 by the weight coefficient of the corresponding marker 62, and generates the representative point reference position information including the reference position of the representative point. The three-dimensional coordinates represented by the reference position information for each of the plurality of markers 62 are acquired by the reference position information acquisition unit 51. Here, in this embodiment, position information of a weighted center of each position represented by the reference position information of the plurality of markers 62 is representative point reference position information. The representative point reference position information is generated as three-dimensional coordinates.

That is, assuming that coordinates of n markers 62 are ($X_n$, $Y_n$, $Z_n$), the number of markers 62 is N, and weight coefficients of the n-th marker 62 are $W_n$, reference position information ($X_{Ga}$, $Y_{Ga}$, $Z_{Ga}$) representing a reference position of a representative point $G_a$ can be computed by the following Equations (1a) to (1c).

$$X_{Ga} = (X_1 W_1 + X_2 W_2 + X_3 W_3 + \ldots + X_n W_n)/N \quad (1a)$$

$$Y_{Ga} = (Y_1 W_1 + Y_2 W_2 + Y_3 W_3 + \ldots + Y_n W_n)/N \quad (1b)$$

$$Z_{Ga} = (Z_1 W_1 + Z_2 W_2 + Z_3 W_3 + \ldots + Z_n W_n)/N \quad (1c)$$

The relative position information computation unit 53 generates relative position information using a position represented by the representative point reference position information as a base point for the position represented by the reference position information of the specific portion 61. The reference position information of the specific portion 61 is acquired by the reference position information acquisition unit 51 as three-dimensional coordinates, and the representative point reference position information is generated by the representative point reference position information computation unit 52 as three-dimensional coordinates. Therefore, the relative position information computation unit 53 generates the relative position information according to a difference between the three-dimensional coordinates of the position represented by the reference position information of the specific portion 61 and the three-dimensional coordinates of the position represented by the representative point reference position.

The marker position information acquisition unit 54 acquires position information of the plurality of markers 62 at time t different from the reference time after a predetermined time has passed from the reference time. In this process, the marker position information acquisition unit 54 acquires the position information of the plurality of markers 62 at time t from a three-dimensional CT image generated by the radiotherapy equipment 3 like the reference position information of the plurality of markers 62 described above. The position information of the plurality of markers 62 is represented as three-dimensional coordinates.

The representative point position information computation unit 55 generates representative point position information at time t from the position information of the plurality of markers 62 at time t different from the reference time acquired by the marker position information acquisition unit 54. Here, the representative point position information computation unit 55 specifies a weight coefficient for each of the plurality of markers 62 as in the representative point reference position information computation unit 52. In addition, the representative point position information computation unit 55 multiplies the three-dimensional coordinates at time t for each of the plurality of markers 62 by the weight coefficient specified for each of the plurality of markers 62, computes the position of the representative point, and generates representative point position information. The three-dimensional coordinates at time t for each of the plurality of markers 62 are acquired by the marker position information acquisition unit. In this embodiment, the representative point position information computation unit 55 generates the position of a weighted center at time t of the plurality of markers 62 as the representative point position information. The representative point position information is represented as three-dimensional coordinates. A formula used to compute a position of a representative point $G_b$ is similar to the above-described Equation (1).

The specific portion position information computation unit 56 generates position information of the specific portion 61 at time t from the representative point position information generated by the representative point position information computation unit 55 and the relative position information generated by the relative position information computation unit 53. The specific portion position information computation unit 56 generates the position information of the specific portion 61 at time t by adding three-dimensional coordinates of the position represented by the representative position information and three-dimensional coordinates of the relative position represented by the relative position information at time t.

The specific portion position information computation unit 56 transmits the computed position information of the specific portion 61 at time t to the radiotherapy equipment control device 2. Based on the position information, the radiotherapy equipment control device 2 controls the radiotherapy equipment 3. Thereby, based on control of the radiotherapy equipment control device 2, the radiotherapy equipment 3 drives the therapeutic radiation irradiation device 16 using the swing mechanism 15 and controls a shape of an irradiation field of the therapeutic radiation 23 using the MLC 20 so that the therapeutic radiation 23 is radiated to a position of the position information computed by the specific portion position information computation unit 56. The radiotherapy equipment control device 2 controls the emission of the therapeutic radiation 23 using the therapeutic radiation irradiation device 16 after driving the swing mechanism 15 and the MLC 20.

Also, the radiotherapy equipment control device 2 can change a positional relationship between the patient 43 and the therapeutic radiation irradiation device 16 further using the turning drive device 11, the traveling drive device, or the couch drive device 42 of the radiotherapy equipment 3 so that the position of the specific portion 61 is irradiated with the therapeutic radiation 23.

Figure 6:
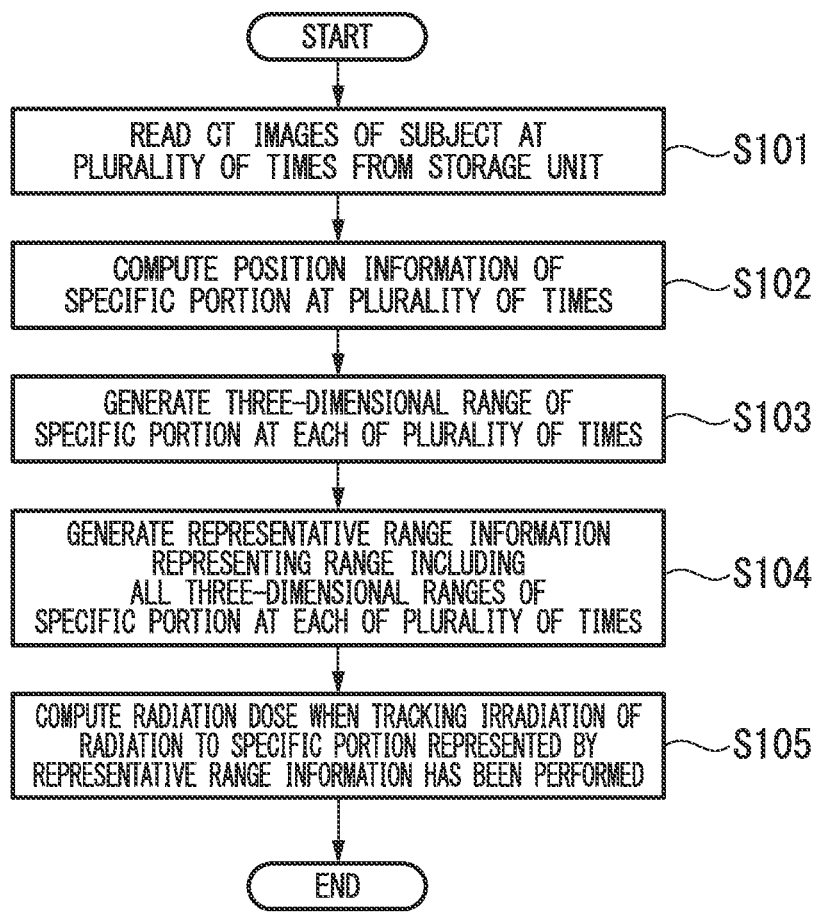
FIG. 6 is a diagram illustrating a processing flow of the treatment planning device 1.

FIG. 6 is a diagram illustrating a processing flow of the treatment planning device 1.

Next, the processing flow of the treatment planning device 1 will be described in order.

First, the treatment planning device 1 stores a CT image of the subject at each of a plurality of times t as time passes in the storage unit 170. The CT image is data generated from a transmission image of the subject captured by the radiotherapy equipment 3. Therefore, when the process starts, the specific portion position computation unit 130 of the treatment planning device 1 reads the CT images of the subject at the plurality of times from the storage unit 170 (step S101). Then, the specific portion position computation unit 130 detects positions of a plurality of markers 62 located in the vicinity of the specific portion 61 from the CT image, and computes position information of the specific portion 61 based on positions of the plurality of markers 62. Likewise, the specific portion position computation unit 130 computes the position information of the specific portion 61 at each time using CT images at a plurality of other times. Thereby, the specific portion position computation unit 130 computes the position information of the specific portion 61 at the plurality of times as time passes (step S102). The position of the marker 62 and the position of the specific portion 61 is represented by three-dimensional coordinates.

Figure 7:
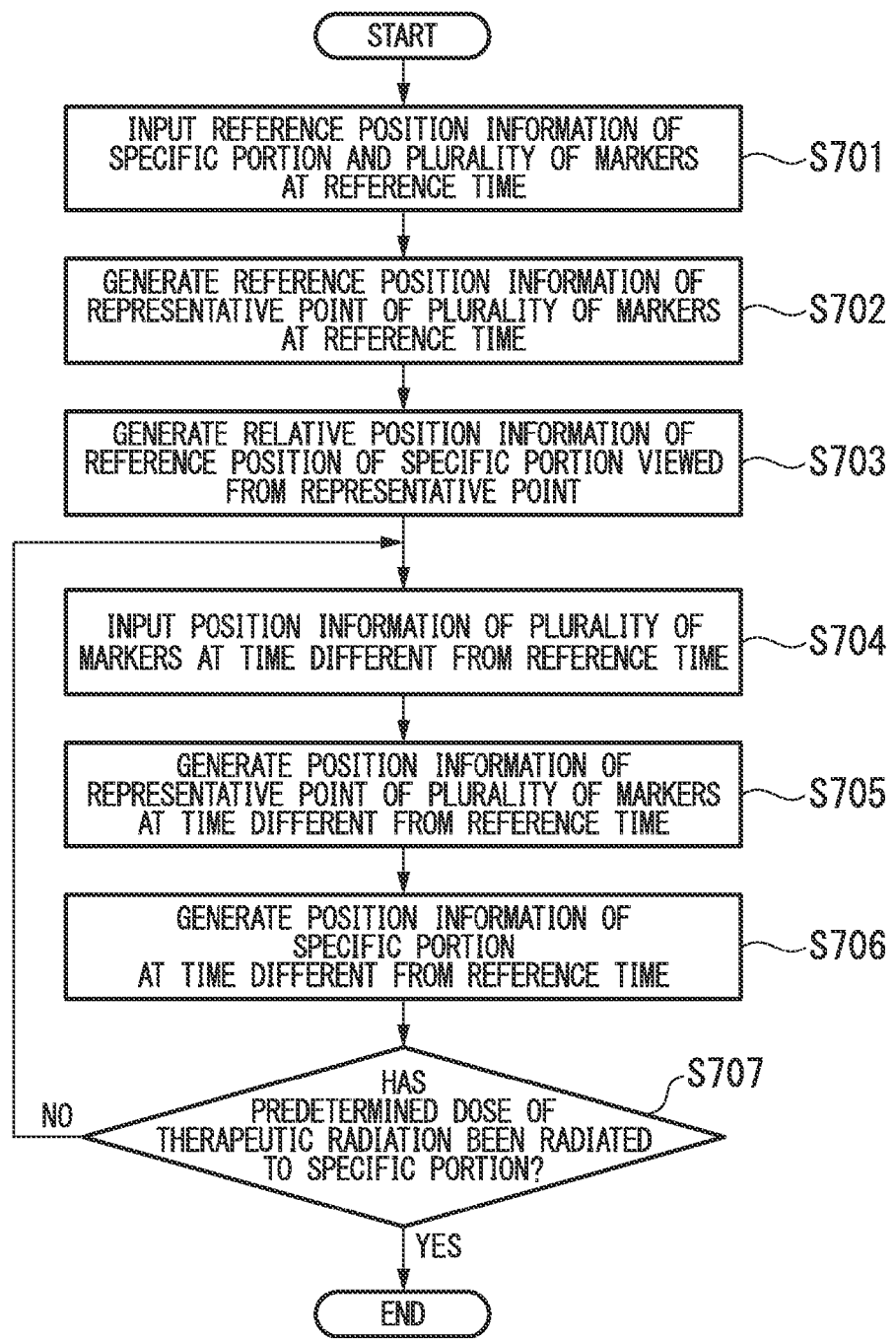
FIG. 7 is a first diagram illustrating a flowchart of a process of the specific portion position computation unit 130.

FIG. 7 is a first diagram illustrating the flowchart of the process of the specific portion position computation unit 130.

Here, details of a process in which the above-described specific portion position computation unit 130 computes the position of the specific portion will be described.

The specific portion position computation unit 130 inputs three-dimensional coordinates as reference position information of the specific portion 61 and the plurality of markers 62 based on a three-dimensional CT image based on a three-dimensional CT image read from the storage unit 170 (step S701). Here, the three-dimensional coordinates of the reference position information of the plurality of markers 62 may be input based on coordinates designated by a doctor using an input means such as a mouse from the three-dimensional CT image displayed on a screen. Alternatively, a processing unit may be provided and the three-dimensional coordinates of the reference position information of the plurality of markers 62 may be input from a processing unit used to detect luminance from luminance values of the plurality of markers in the CT image and automatically computing coordinates from the luminance. Likewise, the three-dimensional coordinates of the position information of the specific portion 61 may also be input based on coordinates designated by the doctor using the input means such as the mouse from the three-dimensional CT image displayed on the screen. Alternatively, the three-dimensional coordinates of the position information of the specific portion 61 may automatically determine an image of the specific portion within the three-dimensional CT image consistent with a pre-stored image of the specific portion 61 using the pre-stored image according to image processing such as pattern matching, and coordinates at the center or the like of a range of the specific portion may be input as the position information of the specific portion 61.

The specific portion position computation unit 130 generates representative point reference position information of the plurality of markers 62 at the reference time from three-dimensional coordinates represented by the reference position information of the plurality of markers 62 acquired in step S701 (step S702). The representative point reference position information is represented as three-dimensional coordinates. A specific generation process will be described later.

Next, the specific portion position computation unit 130 generates relative position information of a position represented by the reference position information of the specific portion 61 using the representative point reference position as the base point (step S703). In detail, a difference between the three-dimensional coordinates of the position represented by the representative point reference position and the three-dimensional coordinates of the position represented by the reference position information of the specific portion 61 is obtained.

Next, the specific portion position computation unit 130 inputs the position information of the plurality of markers 62 from the three-dimensional CT image generated from the transmission image captured at time t different from the reference time as in step S701 (step S704). Then, the specific portion position computation unit 130 generates representative point position information of the plurality of markers 62 at time t from the position information of the plurality of markers 62 (step S705). The position information of the plurality of markers 62 is represented as three-dimensional coordinates. A specific generation process of the representative point position information of the plurality of markers 62 will be described later.

The specific portion position computation unit 130 generates position information of the specific portion 61 at time t from the relative position information representing the relative position computed in step S703 and the representative point position information representing the position of the representative point at time t computed in step S705 (step S706). In detail, a position represented by three-dimensional coordinates obtained by adding the three-dimensional coordinates of the position represented by the relative position information to the three-dimensional coordinates of the position represented by the position information of the representative point is generated as the position information of the specific portion 61.

The specific portion position computation unit 130 acquires the position information of the specific portion 61 in this manner, and determines whether the position information of the specific portion 61 has been computed from three-dimensional CT images generated at all times. Then, when the position information of the specific portion 61 has not been computed from the three-dimensional CT images generated at all times, the specific portion position computation unit 130 proceeds to the process of step S704, and iterates a similar position information computation process on the specific portion 61 by inputting the CT image of the next time t. In addition, when the position information of the specific portion 61 has been computed from the three-dimensional CT images generated at all times, the specific portion position computation unit 130 records the position information of the specific portion 61 computed at each time t on the storage unit 170 and notifies the control unit 110 of the end of the process.

Figure 8:
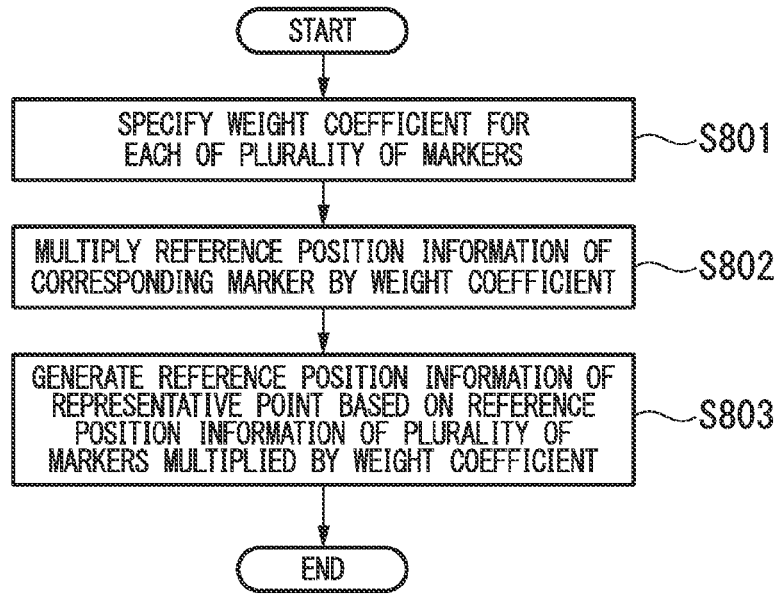
FIG. 8 is a second diagram illustrating a flowchart of a process of the specific portion position computation unit 130.

FIG. 8 is a second diagram illustrating the flowchart of the process of the specific portion position computation unit 130.

Here, the process of computing the reference position information of the plurality of markers 62 in step S702 will be described.

The representative point reference position information computation unit 52 of the specific portion position computation unit 130 computes the reference position information of the representative point at the reference time as illustrated in FIG. 8. First, the representative point reference position information computation unit 52 specifies a weight coefficient for each of the plurality of markers 62 (step S801). Like the position information of the marker 62, this weight coefficient is three-dimensionally specified. That is, the weight coefficient W is represented in the form of ($W_x$, $W_y$, $W_z$). Next, the representative point reference position information computation unit 52 multiplies three-dimensional coordinates of a position represented by the position information of a corresponding marker 62 by the specified weight coefficient (step S802). The representative point reference position information computation unit 52 generates the position information of the representative point based on the three-dimensional coordinates of the position represented by the position information for each of the plurality of markers 62 by which the computed weight coefficient is multiplied (step S803). A formula for computation is similar to the above-described Equation (1a) to (1c). The representative point reference position information computation unit 52 outputs the position information at the reference time of the representative point of the plurality of markers 62 obtained in this manner as the representative point reference position information for the plurality of markers 62 to the relative position information computation unit 53.

Next, the above-described weight coefficient will be described in detail. In this embodiment, the representative point reference position information computation unit 52 computes a reciprocal of a distance between the specific portion 61 and each of the plurality of markers 62 for the plurality of markers 62, and specifies the computed reciprocal as the weight coefficient of each of the plurality of markers 62. The representative point reference position information computation unit 52 obtains distances between the specific portion 61 and the plurality of markers 62 according to absolute values of differences between three-dimensional coordinates of a position represented by the reference position information of the specific portion 61 at the reference time and three-dimensional coordinates of positions represented by reference position information of the plurality of markers 62 at the reference time.

Figure 9:
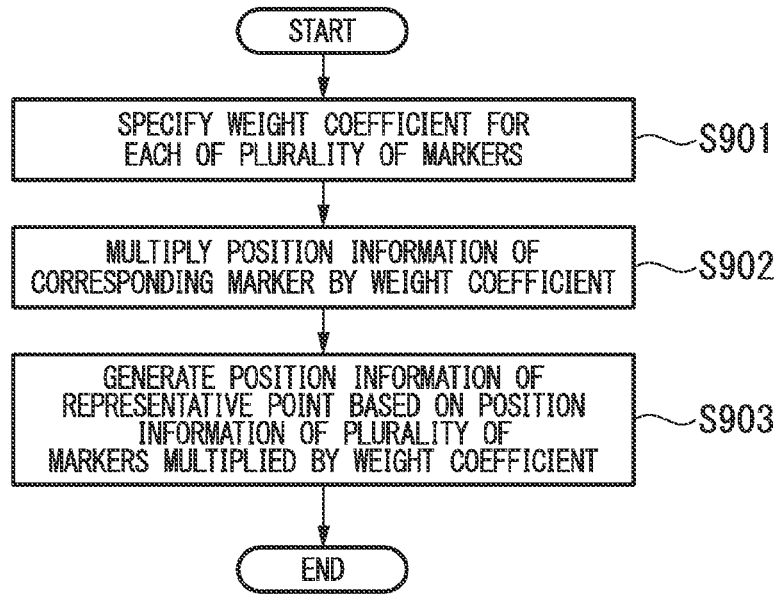
FIG. 9 is a third diagram illustrating a flowchart of a process of the specific portion position computation unit 130.

FIG. 9 is a third diagram illustrating the flowchart of the process of the specific portion position computation unit 130.

Next, the process of computing the position information of the plurality of markers 62 in step S705 will be described. As illustrated in FIG. 9, the representative point position information computation unit 55 of the specific portion position computation unit 130 generates the position information of the representative point at time t. First, the representative point position information computation unit 55 specifies a weight coefficient for each of the plurality of markers 62 (step S901). Like the position information of the marker 62, the weight coefficient is three-dimensionally specified. That is, the weight coefficient W is represented in the form of ($W_x$, $W_y$, $W_z$). Next, the representative point position information computation unit 55 multiplies three-dimensional coordinates of a position represented by the position information of a corresponding marker 62 by the specified weight coefficient (step S902). The representative point position information computation unit 55 generates the position information of the representative point based on the three-dimensional coordinates of the position represented by the position information for each of the plurality of markers 62 by which the computed weight coefficient is multiplied (step S903).

A formula for computation is similar to the above-described Equation (1a) to (1c).

In this embodiment, the representative point position information computation unit 55 computes a reciprocal of a distance between the specific portion 61 and each of the plurality of markers 62 for the plurality of markers 62, and specifies the computed reciprocal as the weight coefficient of each of the plurality of markers 62. In addition, the representative point position information computation unit 55 obtains the weight coefficient at time t from distances between the specific portion 61 and the plurality of markers 62 at the reference time. That is, the representative point position information computation unit 55 obtains the distances between the specific portion 61 and the plurality of markers 62 at the reference time according to absolute values of differences between three-dimensional coordinates of a position represented by the reference position information of the specific portion 61 at the reference time and three-dimensional coordinates of positions represented by reference position information of the plurality of markers 62 at the reference time.

According to this configuration, the treatment planning device 1 can obtain the representative point from position information of the plurality of markers 62 by which weight coefficients corresponding to distances from the specific portion 61 are multiplied through the specific portion position computation unit 130. Thus, the weight coefficient of the marker 62 located at a position away from the specific portion 61 decreases, and the weight coefficient of the marker 62 located at a position close to the specific portion 61 increases. The marker 62 located at the position away from the specific portion 61 is considered to have a displacement amount or displacement direction which is different from that of the specific portion 61 and the marker 62 located at the position close to the specific portion 61 is considered to have a displacement amount or a displacement direction which is similar to that of the specific portion 61. Therefore, because the representative point can be computed by increasing the weight of the marker 62 having a displacement state which is similar to that of the specific portion 61, the state of the displacement of the representative point can be close to the state of the displacement of the specific portion 61. Thereby, it is possible to improve the accuracy of position detection of the specific portion 61. Also, by employing the position information of such a specific portion, it is possible to detect the position of the specific portion with accuracy sufficient for tracking irradiation in the radiotherapy equipment, and it is possible to prevent a normal portion other than the specific portion of the patient from being excessively irradiated with therapeutic radiation.

Also, as the weight coefficient to be applied to each of the plurality of markers 62, correlation parameters between displacement amounts from the reference position for the specific portion 61 and displacement amounts from the reference position for the marker 62 at a plurality of different times may be used.

Here, the correlation parameter is a parameter representing a correlation between the displacement amount from the reference position of the specific portion 61 and the displacement amount from the reference position of the marker 62, and may be computed as a correlation coefficient.

Specifically, the representative point reference position information computation unit 52 or the representative point position information computation unit 55 of the specific portion position computation unit 130 obtains positions represented by position information of the specific portion 61 at a plurality of different times and obtains displacement amounts from the reference position. Likewise, the representative point reference position information computation unit 52 or the representative point position information computation unit 55 of the specific portion position computation unit 130 obtains positions represented by the position information of the marker 62 at a plurality of different times which are the same as when the position of the specific portion 61 is obtained, and obtains displacement amounts from the reference position. The representative point reference position information computation unit 52 or the representative point position information computation unit 55 of the specific portion position computation unit 130 computes a correlation coefficient using the displacement amount from the reference position of the specific portion 61 and the displacement amount from the reference position for each of the markers 62 obtained as described above as two variables. As the correlation coefficient approaches 0, it signifies that there is no correlation between the two variables, and as the correlation coefficient approaches 1, it signifies that the correlation between the two variables is high. The representative point reference position information computation unit 52 or the representative point position information computation unit 55 specifies the computed correlation coefficient as the correlation parameter and uses the specified correlation coefficient as the weight coefficient.

Figures 10, 11:
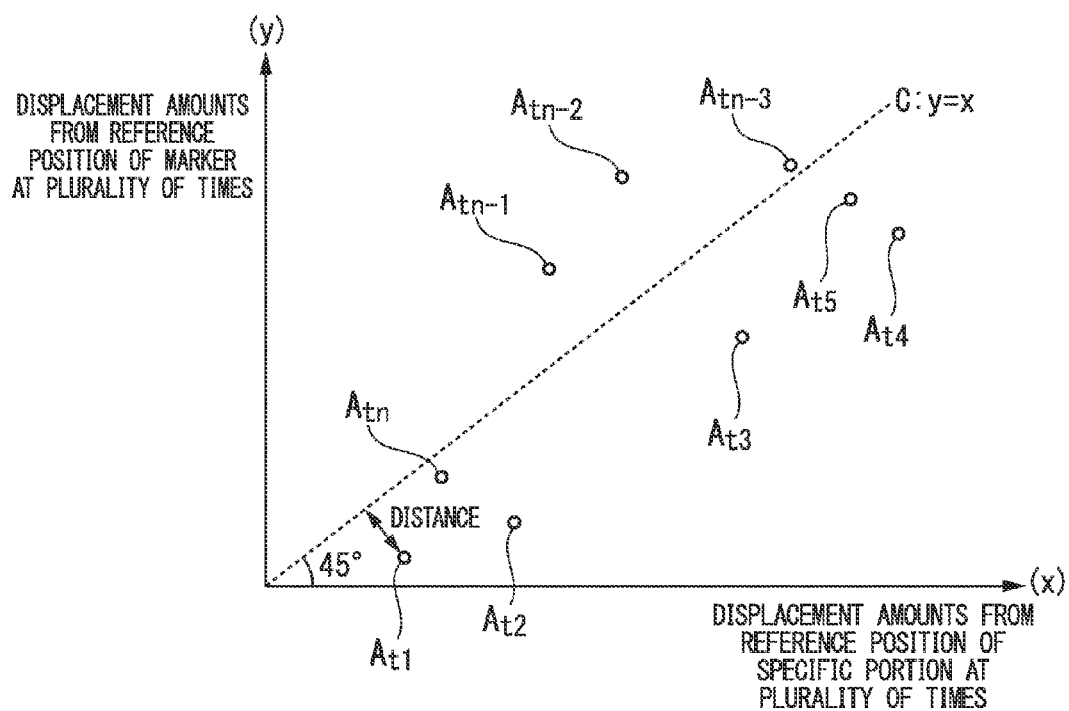
FIG. 10 is a diagram illustrating an example of a relative parameter computation method.
FIG. 11 is a diagram illustrating a correspondence relationship between a displacement amount from a reference position of a specific portion and a displacement amount from a reference position of a marker.

In addition, FIG. 10 is a diagram illustrating an example of a computation method of a relative parameter, and is a diagram illustrating relationships between displacement amounts from a reference position of the specific portion at each of a plurality of times and displacement amounts from a reference position of the marker at each of the plurality of times. As illustrated in FIG. 10, a correlation parameter may be computed based on the displacement amounts from the reference position of the specific portion 61 at a plurality of different times and used as a weight coefficient.

Specifically, as illustrated in FIG. 10, the representative point reference position information computation unit 52 or the representative point position information computation unit 55 of the specific portion position computation unit 130 computes the displacement amounts from the reference position of the specific portion 61 at the plurality of different times and displacement amounts from the reference position of the marker 62 at the plurality of different times. In FIG. 10, $A_t$ represents a correspondence between a displacement amount from the reference position of the specific portion 61 and a displacement amount from a reference position of one certain marker 62a at time t. For example, $A_{t1}$ represents a correspondence between a displacement amount $x_1$ from the reference position of the specific portion 61 and a displacement amount $y_1$ from the reference position of one certain marker 62a at time $t_1$. In addition, $A_{t2}$ represents a correspondence between a displacement amount $x_2$ from the reference position of the specific portion 61 and a displacement amount $y_2$ from the reference position of one certain marker 62a at time $t_2$.

Next, the representative point reference position information computation unit 52 or the representative point position information computation unit 55 of the specific portion position computation unit 130 computes the distance between $A_t(x, y)$ and a straight line represented by y=x. Also, the straight line of y=x corresponds to a line connecting a set of $A_t(x, y)$ when the displacement amount x from the reference position of the specific portion 61 and the displacement amount y from a reference position of one certain marker 62a are the same at each of different times t. The representative point reference position information computation unit 52 or the representative point position information computation unit 55 of the specific portion position computation unit 130 computes distances between a plurality of $A_t(x, y)$ and the straight line represented by y=x for the marker 62a, and computes a sum of the distances. Then, a reciprocal of the sum is specified as a correlation parameter and specified as a weight coefficient for the marker 62a. In addition, similar weight coefficient specification is also performed for markers 62 other than the marker 62a.

FIG. 11 is a diagram illustrating a correspondence between a displacement amount from a reference position of a specific portion and a displacement amount from a reference position of a marker.

As illustrated in FIG. 11, a displacement amount from a reference position of the specific portion 61 and a displacement amount from a reference position of one certain marker 62a can be represented by a plot $A_{tn}$ (n=1, 2, . . . , n) as illustrated at each time to (n=1, 2, . . . , n). The representative point reference position information computation unit 52 or the representative point position information computation unit 55 computes a distance between a straight line C having a tilt of 45 degrees formed from a set of plots in which the displacement from the reference position of the specific portion 61 is equal to the displacement from the reference position of the marker 62 and a plot $A_{t1}$, similarly computes a distance of the plot $A_{tn}$ (n=1, 2, . . . , n) from the straight line C, and further computes a sum of the distances. As the sum of the distances increases, the displacement amount of the marker 62a is represented to be different from the displacement amount of the specific portion 61.

In contrast, as the sum of the distances decreases, the displacement amount of the marker 62a is represented to be similar to the displacement amount of the specific portion 61. The representative point reference position information computation unit 52 or the representative point position information computation unit 55 specifies a reciprocal of the sum as a weight coefficient to be applied to the marker 62a. In addition, likewise, the representative point reference position information computation unit 52 or the representative point position information computation unit 55 specifies weight coefficients for other markers.

According to this configuration, it is possible to obtain a representative point by multiplying a high weight coefficient with respect to a marker 62 representing a high correlation with the specific portion 61. Thus, a displacement state of the representative point can approach a displacement state of the specific portion 61, and the accuracy of position detection of the specific portion 61 can be improved.

In addition, when the displacement state is different even when the marker 62 is located in the vicinity of the specific portion 61, for example, even when the marker 62 is located in the vicinity of a heart of a subject and significantly affected by the pulsation of the heart, etc., it is possible to accurately detect the position of the specific portion 61.

In addition, the above-described weight coefficient may be specified by an arbitrary input by the user through the input means.

According to this configuration, it is possible to arbitrarily specify weight coefficients of the plurality of markers 62 through the user's determination. Therefore, it is possible to more simply detect the position of the specific portion 61 using a representative point to which a weight is assigned for each of the plurality of markers 62.

In addition, a weight coefficient of at least one marker 62 among the plurality of markers 62 may be specified as 0.

According to this configuration, it is possible to exclude a marker 62 having an obviously different displacement state from the specific portion 61 or a marker 62 determined to be improper for use in position detection of the specific portion 61 for any reason from subsequent computation for the position detection of the specific portion 61. Thereby, it is possible to more accurately detect the position of the specific portion 61.

Also, a marker 62 to be used for compute the position detection of the specific portion 61 can be arbitrarily selected in place of identifying the weight coefficient of at least one marker 62 among the plurality of markers 62 as 0.

Although the above-described process of computing position information of the specific portion 61 is a computation using the center of gravity, the computation of the position information of the specific portion 61 may be performed using the distance between the marker 62 and the specific portion 61 in place thereof. The process of computing the position information of the specific portion 61 according to the method is as follows.

(1) Positions of the specific portion 61 and each marker 62 are acquired at the reference time.

(2) Positions of each marker 62 at other times are acquired.

(3) Fluctuation of distances at the other times from the distance at the reference time is evaluated based on distances between the positions of each marker 62 and the positions of the specific portion at the other times and a distance between the position of each marker 62 and the position of the specific portion at the reference time.

(4) The position information of the specific portion having a distance fluctuation error according to a least squares method is computed as the position information of the specific portion at a certain time.

Therefore, after the position information of the specific portion 61 is computed according to the process as describe above, the control unit 110 notifies the specific portion range information generation unit 140 of the process start. Then, the specific portion range information generation unit 140 generates a three-dimensional range (critical tumor volume (CTV)) of the specific portion at each of the plurality of times (step S103).

More specifically, the specific portion range information generation unit 140 first displays a CT image of time t1 read from the storage unit 170 on the screen. The CT image includes a plurality of images of cross sections of the subject. In the plurality of images of cross sections of the subject represented by the CT image of time t1 displayed on the screen, a user such as a doctor encircles and writes a range of the specific portion. The written information is detected by an input sensor such as a touch panel constituting the screen and output to the treatment planning device 1. Thereby, the specific portion range information generation unit 140 inputs range information of the specific portion in each cross section represented by the CT image of time t1 and generates information of a three-dimensional range of the specific portion based on the input information. Alternatively, the specific portion range information generation unit 140 may be configured to generate the information of the three-dimensional range of the specific portion according to pattern matching or the like based on the pre-stored information of the image of the specific portion.

Therefore, when the generation of the information of the three-dimensional range of the specific portion is completed at time t1, the specific portion range information generation unit 140 determines whether three-dimensional range information for CT images of all times t has been generated. Then, when the three-dimensional range information for the CT images of all times t is not generated, the CT image of the next time t is read from the storage unit 170. Likewise, a plurality of images of each cross section of the CT image are output to the screen. Thereby, the specific portion range information generation unit 140 iterates the generation of the three-dimensional range information for the CT images of all times t. In addition, upon generating the three-dimensional range information for the CT images of all times t stored in the storage unit 170, the specific portion range information generation unit 140 notifies the control unit 110 of the process completion.

Next, the control unit 110 instructs the specific portion representative range information generation unit 150 to start the process. Then, the specific portion representative range information generation unit 150 generates representative range information representing a range including all three-dimensional ranges of the specific portion at each of a plurality of times t when the position information of the specific portion at each of the plurality of times t is designated as the same reference point (step S104).

More specifically, the specific portion representative range information generation unit 150 reads the position (three-dimensional coordinates) of the specific portion of each time t and the information of the three-dimensional range of the specific portion of each time t from the storage unit 170. Then, the specific portion representative range information generation unit 150 aligns the position information of the specific portion of each time t as the same reference point. In this case, the specific portion representative range information generation unit 150 generates representative range information representing a range including all three-dimensional ranges.

Figure 12:
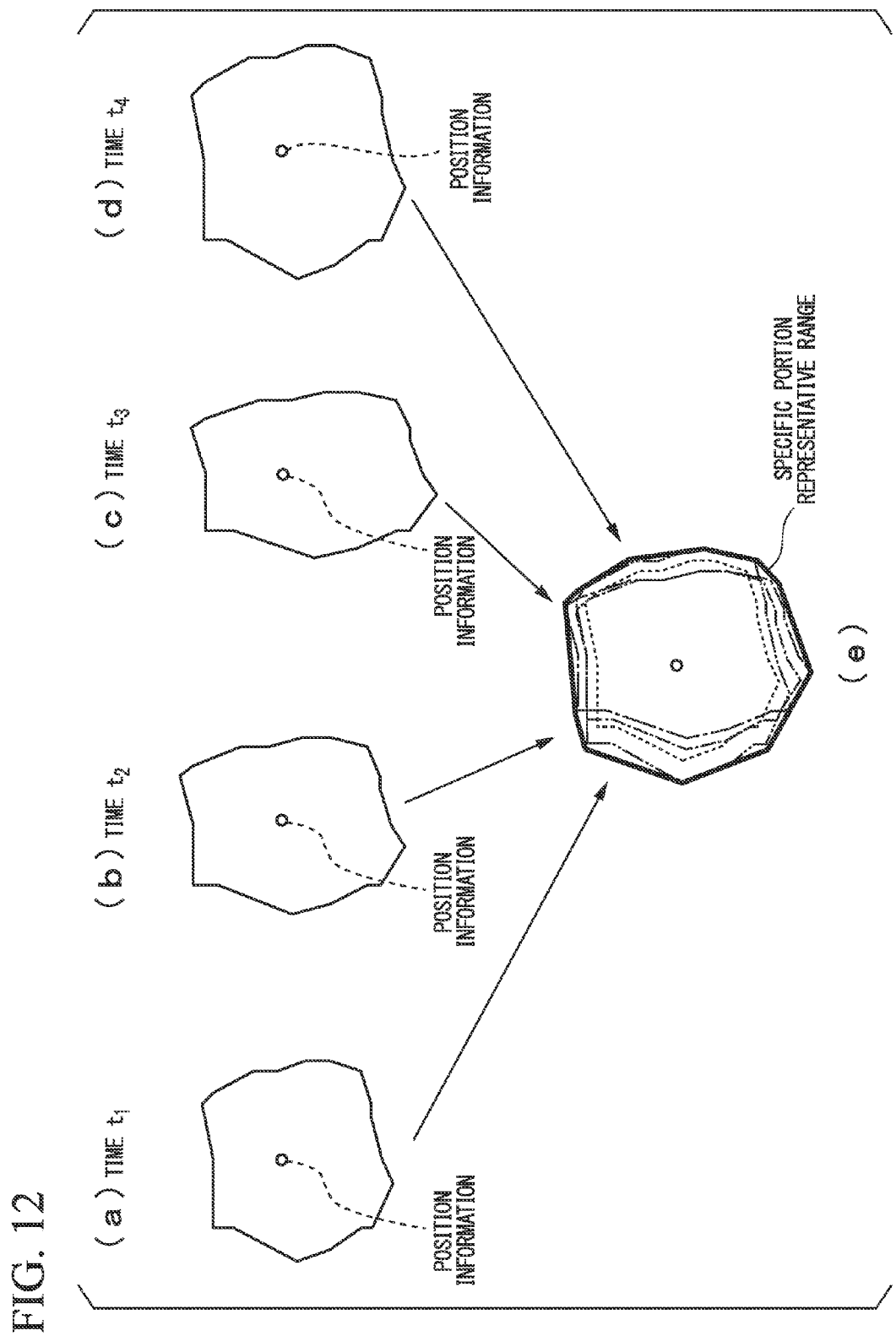
FIG. 12 is a diagram illustrating a processing outline of a specific portion representative range information generation unit 150.

FIG. 12 is a diagram illustrating a processing outline of the specific portion representative range information generation unit 150.

In FIG. 12, (a) illustrates three-dimensional range information for a CT image of time $t_1$, (b) illustrates three-dimensional range information for a CT image of time $t_2$, (c) illustrates three-dimensional range information for a CT image of time $t_3$, and (d) illustrates three-dimensional range information for a CT image of time $t_4$. The three-dimensional range information of (a) to (d) may include three-dimensional position information of the specific portion at each time t. Because the specific portion moves within the subject as time passes and the range of the specific portion is deformed, the three-dimensional range information of (a) to (d) represents information such as three-dimensional coordinates representing different position information or ranges.

Then, as illustrated in (e) of FIG. 12, the specific portion representative range information generation unit 150 aligns the position information of the specific portion of each time t as the same reference point. In this case, the specific portion representative range information generation unit 150 generates representative range information representing a range including all three-dimensional ranges. The range of the outermost bold line of (e) of FIG. 12 is a range representing the representative range information. Then, the specific portion representative range information generation unit 150 records the generated representative range information on the storage unit 170 and notifies the control unit 110 of the end of the process. Also, although (a) to (e) in FIG. 12 two-dimensionally illustrate the range of the specific portion, information representing a three-dimensional range is actually provided.

Next, the control unit 110 instructs the radiation dose computation unit 160 to start the process. Then, the radiation dose computation unit 160 acquires representative range information of the specific portion recorded on the storage unit 170. Then, the radiation dose computation unit 160 computes a radiation dose when radiation to the specific portion represented by the representative range information is tracked and radiated (step S105). Also, although the radiation dose computation unit 160 computes a radiation dose using a strength of radiation to be radiated, an irradiation time, a position of a radiation source, representative range information, etc., it is only necessary to use the known technology as a technique of this process. Alternatively, the radiation dose computation unit 160 may be configured to compute an irradiation time using the known technology until a radiation dose capable of being radiated to the specific portion reaches an upper limit. Also, at this time, the user such as the doctor may input information such as the position of the radiation source to the treatment planning device 1. The user such as the doctor develops a treatment plan regarding the position of the radiation source, the irradiation time, etc. using the computed radiation dose.

Although the embodiment of the present invention has been described above, the radiation dose to be radiated to the specific portion of the range represented by the representative range information is computed using the three-dimensional representative range information including all range of the specific portion (affected part) to be moved and deformed according to time by the process of the above-described treatment planning device. Thereby, it is possible to determine an irradiation range of radiation so that radiation exposure outside of the specific portion does not occur and compute a radiation dose more accurately than in the past when radiation exposure outside of the specific portion of the radiation does not occur.

Also, the treatment planning device outputs the above-described representative range information to the radiotherapy equipment control device 2.

Then, the radiotherapy equipment control device 2 outputs the representative range information to the therapeutic radiation irradiation device 16. Then, the therapeutic radiation irradiation device 16 controls the shape of the MLC 20 based on representative range information. That is, the MLC 20 changes a shape of a radiation field when the therapeutic radiation 23 is radiated to the patient by shielding part of the therapeutic radiation 23.

Each process of the above-described treatment planning device 1 may be configured to be performed by the radiotherapy equipment control device 2 having each processing unit which is similar to that of the treatment planning device 1 and performed by the radiotherapy equipment 3 having each processing unit which is similar to that of the treatment planning device 1.

Each device described above internally includes a computer system. Further, the steps of each of the above-described processes are stored in a program format on a computer-readable recording medium, and the above-described processes runs by causing a computer to reads and executes the program. The computer-readable recording medium refers to a magnetic disk, a magneto-optical disc, a compact disc-read only memory (CD-ROM), a digital versatile disc (DVD)-ROM, a semiconductor memory, or the like. The computer program may be configured to be distributed to a computer via a communication circuit and executed by the computer receiving the distribution.

In addition, the above-described program may be used to implement some of the above-described functions.

Further, the above-described program may also be a program capable of implementing the above-described functions in combination with a program already recorded on the computer system, that is, a so-called differential file (differential program).

INDUSTRIAL APPLICABILITY

According to an aspect of the present invention, it is possible to provide a treatment planning device capable of more accurately measuring movement within a subject or a radiation dose of the specific portion of a range change as time passes.

DESCRIPTION OF THE REFERENCE SYMBOLS

1 Treatment planning device
2 Radiotherapy equipment control device
3 Radiotherapy equipment
110 Control unit
120 Communication unit
130 Specific portion position computation unit
140 Specific portion range information generation unit
150 Specific portion representative range information generation unit
160 Radiation dose computation unit
51 Reference position information acquisition unit
52 Representative point reference position information computation unit
53 Relative position information computation unit
54 Marker position information acquisition unit
55 Representative point position information computation unit
56 Specific portion position information computation unit

The invention claimed is:

1. A treatment planning device that specifies a position of a specific portion within a subject and computes a radiation dose to be radiated to the specific portion, the treatment planning device comprising:
    a specific portion position computation unit configured to compute position information of the specific portion at a plurality of times as time passes based on positions of a plurality of markers located in the vicinity of the specific portion;
    a specific portion range information generation unit configured to generate a three-dimensional range of the specific portion at each of the plurality of times;
    a specific portion representative range information generation unit configured to generate representative range information representing a range including all the three-dimensional ranges of the specific portion at each of the plurality of times when the position information of the specific portion at each of the plurality of times is designated as the same reference point; and
    a radiation dose computation unit configured to compute a radiation dose to be radiated to the range of the specific portion represented by the representative range information when radiation is radiated to the range of the specific portion represented by the representative range information for a predetermined time by following the position information of the specific portion at each of the plurality of times, wherein the specific portion position computation unit generates the position information of the specific portion at the plurality of times, which changes as time passes, based on reference position information of the specific portion, which is designated by using position information of a representative point of the plurality of markers as a base point, and position information of the plurality of markers that changes as time passes.

2. The treatment planning device according to claim 1, wherein the specific portion position computation unit includes:
- a reference position information acquisition unit configured to acquire reference position information representing a position within the subject at a reference time of each of the specific portion and the plurality of markers;
- a representative point reference position information computation unit configured to generate reference position information representing a position within the subject at the reference time of a representative point of the plurality of markers from the reference position information of the plurality of markers;
- a relative position information computation unit configured to generate relative position information using a position represented by the reference position information of the representative point as a base point for a position represented by the reference position information of the specific portion;
- a marker position information acquisition unit configured to acquire position information of the plurality of markers within the subject at another time different from the reference time;
- a representative point position information computation unit configured to generate position information of the representative point within the subject at the other time of the plurality of markers from the position information of the plurality of markers; and
- a specific portion position information computation unit configured to generate position information of the specific portion at the other time from the position information of the representative point and the relative position information.

3. The treatment planning device according to claim 2, wherein the representative point reference position information computation unit specifies a weight coefficient for each of the plurality of markers and generates the reference position information of the representative point based on the position information of the plurality of markers weighted by the weight coefficient, and wherein the representative point position information computation unit generates the position information of the representative point based on the position information of the plurality of markers weighted by the weight coefficient.

4. A processing method of a treatment planning device that specifies a position of a specific portion within a subject and computes a radiation dose to be radiated to the specific portion, the processing method of a treatment planning device comprising:
- computing, by a specific portion position computation unit, position information of the specific portion at a plurality of times as time passes based on positions of a plurality of markers located in the vicinity of the specific portion;
- generating, by a specific portion range information generation unit, a three-dimensional range of the specific portion at each of the plurality of times;
- generating, by a specific portion representative range information generation unit, representative range information representing a range including all the three-dimensional ranges of the specific portion at each of the plurality of times when the position information of the specific portion at each of the plurality of times is designated as the same reference point; and
- computing, by a radiation dose computation unit, a radiation dose to be radiated to the range of the specific portion represented by the representative range information when radiation is radiated to the range of the specific portion represented by the representative range information for a predetermined time by following the position information of the specific portion at each of the plurality of times, wherein the specific portion position computation unit generates the position information of the specific portion at the plurality of times, which changes as time passes, based on reference position information of the specific portion, which is designated by using position information of a representative point of the plurality of markers as a base point, and position information of the plurality of markers that changes as time passes.

5. A non-transitory computer-readable storage medium storing a computer program, which when executed by a processor in a treatment planning device that specifies a position of a specific portion within a subject and computes a radiation dose to be radiated to the specific portion, causes the treatment planning device to function as:
- a specific portion position computation means configured to compute position information of the specific portion at a plurality of times as time passes based on positions of a plurality of markers located in the vicinity of the specific portion;
- a specific portion range information generation means configured to generate a three-dimensional range of the specific portion at each of the plurality of times;
- a specific portion representative range information generation means configured to generate representative range information representing a range including all the three-dimensional ranges of the specific portion at each of the plurality of times when the position information of the specific portion at each of the plurality of times is designated as the same reference point; and
- a radiation dose computation means configured to compute a radiation dose to be radiated to the range of the specific portion represented by the representative range information when radiation is radiated to the range of the specific portion represented by the representative range information for a predetermined time by following the position information of the specific portion at the plurality of times, wherein the specific portion position computation means generates the position information of the specific portion at the plurality of times, which changes as time passes, based on reference position information of the specific portion, which is designated by using position information of a representative point of the plurality of markers as a base point, and position information of the plurality of markers that changes as time passes.

* * * * *